(12) United States Patent
Evans et al.

(10) Patent No.: US 12,144,887 B2
(45) Date of Patent: Nov. 19, 2024

(54) GUIDING MUSCULOSKELETAL PROCEDURES

(71) Applicant: Agitated Solutions Inc., Oakdale, MN (US)

(72) Inventors: Morgan Evans, Apple Valley, MN (US); Kenneth Trauner, San Francisco, MN (US)

(73) Assignee: Agitated Solutions Inc., St. Paul, MN (US)

( * ) Notice: Subject to any disclaimer, the term of this patent is extended or adjusted under 35 U.S.C. 154(b) by 24 days.

(21) Appl. No.: 17/568,610

(22) Filed: Jan. 4, 2022

(65) Prior Publication Data

US 2022/0202702 A1 Jun. 30, 2022

Related U.S. Application Data

(63) Continuation-in-part of application No. 17/322,061, filed on May 17, 2021.

(60) Provisional application No. 63/133,657, filed on Jan. 4, 2021, provisional application No. 63/026,198, filed on May 18, 2020.

(51) Int. Cl.
*A61B 5/05* (2021.01)
*A61K 9/00* (2006.01)
*A61P 19/02* (2006.01)

(52) U.S. Cl.
CPC ............ *A61K 9/0019* (2013.01); *A61P 19/02* (2018.01)

(58) Field of Classification Search
CPC .............................. A61K 9/0019; A61P 19/02
See application file for complete search history.

(56) References Cited

U.S. PATENT DOCUMENTS

| 2006/0041243 | A1* | 2/2006 | Nayak ............... A61B 17/0206 604/173 |
| 2006/0100514 | A1 | 5/2006 | Lopath |
| 2007/0239027 | A1 | 10/2007 | Nita |

(Continued)

FOREIGN PATENT DOCUMENTS

CN 102917656 2/2013

OTHER PUBLICATIONS

Bernard et al., Agitated Saline Contrast Echocardiography in the Identification of Intra- and Extracardiac Shunts: Connecting the Dots, Journal of the American Society of Echocardiography, 2020, 1-11, doi: 10.1016/j.echo.2020.09.013.

(Continued)

*Primary Examiner* — Joel F Brutus
(74) *Attorney, Agent, or Firm* — Matthew J. Smyth

(57) ABSTRACT

A method may include providing a syringe device having (a) a single needle, (b) a first syringe comprising saline with microbubbles, (c) a second syringe comprising a therapeutic compound, and (d) a connector coupling the single needle to the first syringe and to the second syringe. The method may further include guiding the single needle to an injection site of a patient; injecting, with the first syringe, a quantity of saline with microbubbles; confirming a desired position of the single needle, with ultrasound imaging, by identifying the microbubbles in the quantity of saline relative to a tip of the single needle and further relative to one or more anatomical landmarks visible with the ultrasound imaging; and injecting, with the second syringe, the therapeutic compound at the injection site.

10 Claims, 8 Drawing Sheets

(56) References Cited

U.S. PATENT DOCUMENTS

| | | | |
|---|---|---|---|
| 2010/0228122 A1* | 9/2010 | Keenan | B01F 31/65 604/24 |
| 2011/0152836 A1* | 6/2011 | Riopelle | A61M 25/06 604/510 |
| 2011/0160620 A1 | 6/2011 | Gill | |
| 2011/0201974 A1 | 8/2011 | Soltani | |
| 2013/0324989 A1 | 12/2013 | Leung | |
| 2016/0331434 A1 | 11/2016 | Phillips | |
| 2018/0036033 A1 | 2/2018 | Ignagni | |
| 2018/0071553 A1 | 3/2018 | Vortman | |

OTHER PUBLICATIONS

Cabrelli et al., Stable phantom materials for ultrasound and optical imaging, Physics in Medicine and Biology, 2017, 432-447, doi:10.1088/1361-6560/62/2/432.

Cooley et al., Characterization of the interaction of nanobubble ultrasound contrast agents with human blood components, Bioactive Materials, 2023, 642-652.

Goertz et al., Attenuation and size distribution measurements of Definity(TM) and manipulated Definity(TM) populations, Ultrasound in Medicine and Biology, 2007, vol. 33, No. 9, 1376-1388, doi: 10.1016/j.ultrasmedbio.2007.03.009.

Kabha and Barak, Paradoxical Symptomatic Air Embolism after Saline Contrast Transesophageal Echocardiography, Echocardiography: A Journal of CV Ultrasound & Allied Tech., 2008, vol. 25, No. 3, 349-350, doi: 10.1111/j. 1540-8175.2007.00628.x.

Kubo and Nakata, Air embolism due to a patent foramen ovale visualized by harmonic contrast enchocardiography, Journal of Neurology, Neurosurgery and Psychiatry, 2001, Neurological Picture, 71:555, doi: 10.1136/jnnp.71.4.555.

Kumar et al., Micro-Bubbles in the Left Heart, Journal of Cardiology & Cardiovascular Therapy, 2017, vol. 8, Issue 5, 1-4, doi:10.19080/JOCCT.2017.08.555748.

Lin et al., Optimizing Sensitivity of Ultrasound Contrast-Enhanced Super-Resolution Imaging by Tailoring Size Distribution of Microbubble Contrast Agent, Ultrasound in Medicine and Biology, 2017, vol. 43, No. 10, 2488-2493, doi:10.1016/j.ultrasmedbio.2017.05.014.

Liu, Weizhen, et al. "A novel injectable, cohesive and toughened si-HPMC (silanized-hydroxypropyl methylcellulose) composite calcium phosphate cement for bone substitution". Acta Biomaterialia, vol. 10, No. 7, 2014, p. 3335-3345. https://doi.org/10.1016/j.actbio.2014.03.009.

MacMahon, Peter, et al. "Injectable corticosteroid and local anesthetic preparations: A review for radiologists". Radiology, vol. 252, No. 3, 2009, p. 647-661. https://doi.org/10.1148/radiol.2523081929.

Denis et al., Randomized Double-Blind Controlled Trial Comparing the Effectiveness of Lumbar Transforaminal Epidural Injections of Particulate and Nonparticulate Corticosteroids for Lumbosacral Radicular Pain, 2015, Pain Medicine, 16: 1697-1708.

* cited by examiner

GUIDING MUSCULOSKELETAL PROCEDURES

CROSS-REFERENCE TO RELATED APPLICATIONS

This application is a continuation-in-part of U.S. application Ser. No. 17/322,061, titled "Guiding Musculoskeletal Procedures," filed on May 17, 2021, which claims the benefit of U.S. Provisional Application Ser. No. 63/026,198, titled "Guiding Musculoskeletal Injections," filed on May 18, 2020; and this application claims the benefit of U.S. Provisional Application Ser. No. 63/133,657, titled "Musculoskeletal Orbis Contrast Device," filed on Jan. 4, 2021. This application incorporates the entire contents of the foregoing application herein by reference.

TECHNICAL FIELD

Various embodiments relate generally to providing relief for musculoskeletal conditions.

BACKGROUND

Injection therapy for intra- and extra-articular structures is available for musculoskeletal pain and is a regular component of rheumatology, orthopedics, sports medicine, anesthesia, physical medicine and rehabilitation, and general practice.

Joint aspiration is one exemplary procedure to remove fluid from the space around a joint. It is typically performed using a needle and a syringe, often under local anesthetic, to relieve swelling or to obtain fluid for analysis, to diagnose joint orders or issues. Joint aspiration is most commonly performed on a knee, but it may also be performed on a hip, ankle, shoulder, elbow or wrist.

In some instances, an injection may be provided following the joint aspiration; in other instances, an injection in or around a joint may be provided as a stand-alone therapy for a joint issue. Corticosteroids (e.g., hydrocortisone, methylprednisolone, triamcinolone, dexamethasone), local anesthetics (e.g., lidocaine, bupivacaine), saline, hyaluronic acid, or other compounds may be injected to provide relief from joint issues.

Opportunity exists to reduce the level of expertise needed to perform injections and improve the accuracy of needle placement. In one survey of general practitioners, 95% of respondents considered themselves inadequately trained for musculoskeletal injections, and 89% indicated that they would refer their patients to specialty clinics for these injections (resulting, in many cases, in long delays to patients receiving therapy). This reluctance among general practitioners to provide musculoskeletal injection therapies may be because an inappropriately placed injection can result in insufficient medical treatment, as well as increased pain, morbidity and procedure times.

SUMMARY

In some implementations, a device can deliver air microbubbles mixed in saline or analgesic cocktails, to both increase the access and accuracy of ultrasound-guided musculoskeletal injection procedures. Such implementations can benefit novice and expert ultrasound-guided musculoskeletal injection caregivers alike, which may result in more general practitioners and even mid-level providers (e.g., nurse practitioners and physician assistants) being able to perform joint injections for pain relief—potentially bringing faster relief to a greater number of patients than is currently possible. In addition, such implementations may improve injection accuracy, reduce patient pain, result in fewer complications, consume fewer healthcare resources, and boost confidence of care providers in delivering therapy.

In some implementations, a device can be employed to instantaneously produce microbubble air/saline mixtures or analgesic cocktails as a low cost, effective contrast agent for confirmation of needle placement during ultrasound-guided musculoskeletal injections. Such a device may simplify musculoskeletal injections by (i) providing a controlled mixture of air bubbles as a low cost, safe contrast agent; (ii) providing a contrast agent that dissipates quickly in instances of an inaccurate placement; (iii) enhancing ease-of-use by providing a sleek and light form factor; and (iv) allowing a caregiver to inject contrast in combination with a therapeutic or anesthetic cocktail, in many cases eliminating further needle manipulation (e.g., to switch syringes, as is currently required in other implementations). A caregiver may employ a device like the devices described herein between a standard, drug-filled syringe, and a needle. As the syringe is de-plunged, the device may inject air microbubbles into the fluid stream. If the needle is placed in tissue (e.g., outside of the intended injection region), the microbubbles may quickly dissipate, restoring ultrasound visibility and allowing the user to reposition the needle; if the needle is placed correctly, the microbubbles may delineate the edges of the joint or illuminate tissue layers for confirmation of location or for diagnosis of conditions like effusion.

In some implementations, a method includes providing a syringe device having (a) a single needle, (b) a first syringe comprising saline with microbubbles, (c) a second syringe comprising a therapeutic compound, and (d) a connector coupling the single needle to the first syringe and to the second syringe. The method may further include guiding the single needle to an injection site of a patient; injecting, with the first syringe, a quantity of saline with microbubbles; confirming a desired position of the single needle, with ultrasound imaging, by identifying the microbubbles in the quantity of saline relative to a tip of the single needle and further relative to one or more anatomical landmarks visible with the ultrasound imaging; and injecting, with the second syringe, the therapeutic compound at the injection site.

In some implementations, the therapeutic compound comprises a corticosteroid. In some implementations, the therapeutic compound comprises lidocaine.

In some implementations, a method includes providing a syringe device having (a) a single needle, (b) a first syringe comprising saline with microbubbles, (c) a second syringe configured to aspirate fluid from a treatment site of a patient, and (d) a connector coupling the single needle to the first syringe and to the second syringe. The method may further include guiding the single needle to the treatment site; injecting, with the first syringe, a quantity of saline with microbubbles; confirming a desired position of the single needle, with ultrasound imaging, by identifying the microbubbles in the quantity of saline relative to a tip of the single needle and further relative to one or more anatomical landmarks visible with the ultrasound imaging; and aspirating, with the second syringe, fluid from the treatment site.

In some implementations, a method includes providing a syringe device having (a) a single needle, (b) a first syringe comprising saline with microbubbles and having a first-syringe plunger, (c) a second syringe having a second-syringe plunger that is independently operable relative to the first-syringe plunger, and (d) a connector coupling the single needle to the first syringe and to the second syringe. The method may further include guiding the single needle to a treatment site of a patient; injecting, with the first syringe, a quantity of saline with microbubbles; confirming a desired position of the single needle, with ultrasound imaging, by identifying the microbubbles in the quantity of saline relative to a tip of the single needle and further relative to one or more anatomical landmarks visible with the ultrasound imaging; and with the second syringe, injecting a therapeutic compound at the treatment site or aspirating fluid from the treatment site.

Injecting with the first syringe may include depressing the first-syringe plunger. The second syringe may include a therapeutic compound, and injecting the therapeutic compound may include depressing the second-syringe plunger. The second syringe may be configured to aspirate fluid from a treatment site of a patient, and aspirating fluid from the treatment site may include drawing back the second-syringe plunger.

DETAILED DESCRIPTION

Figure 1A:
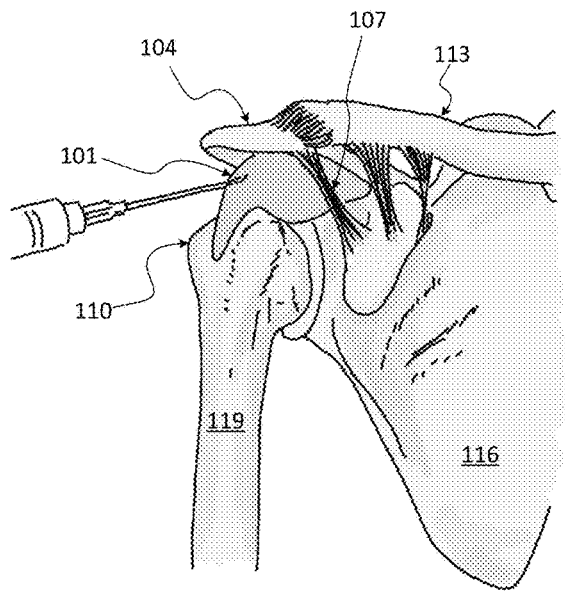
FIG. 1A depicts an exemplary injection into a subacromial bursa.

In some implementations, a device can deliver air microbubbles mixed in saline or analgesic cocktails, to both increase the access and accuracy of ultrasound-guided musculoskeletal injection procedures. Such implementations can benefit novice and expert ultrasound-guided musculoskeletal injection caregivers alike, which may result in more general practitioners and even mid-level providers (e.g., nurse practitioners and physician assistants) being able to perform joint injections for pain relief—potentially bringing faster relief to a greater number of patients than is currently possible. In addition, such implementations may improve injection accuracy, reduce patient pain, result in fewer complications, consume fewer healthcare resources, and boost confidence of care providers in delivering therapy.

As a more specific example, a variety of injuries and conditions can affect joints, causing swelling, pain, loss of mobility, and other issues. For many of these conditions, aspiration of joint fluid may be indicated; an injection of a local anesthetic, corticosteroid or other compound may provide relief; or some other orthopedic or musculoskeletal procedure may be indicated.

Aspirations and injections are both typically performed with needles and syringes. Because of the complex structures that surround most joints (skeletal structures, vessels, nerves, bursa, ligaments, tendons, etc.), it is critical that any needle used to aspirate or deliver a therapeutic compound is properly placed relative to the surrounding structures.

Failure to properly position a needle or deliver a corticosteroid or other compound to other than an intended space or structure can have very serious effects. For example, in some cases, misapplication of a corticosteroid can result in neuritis (minor irritation to nerves), thinning of the bones (osteoporosis), avascular necrosis (serious damage to the bones of the large joints), tissue damage or tendon rupture, septic arthritis, necrotizing fasciitis, osteomyelitis, spinal cord or peripheral nerve injuries, or other serious complications. Given the number of different joints that may be treated, and the various indications for aspiration or delivery of a corticosteroid or other compound, any tools or aids for needle positioning can lower procedure risk.

Image-based guidance may be employed in many procedures. For example, ultrasound and x-ray fluoroscopy are often employed; and in some cases, computed tomography (CT) or magnetic resonance imaging (MRI) guidance may be employed. X-ray fluoroscopy typically exposes a patient to high levels of radiation; and CT and Mill guidance require specialized equipment that can greatly limit the range of movement for both patient and physician during a procedure. Ultrasound guidance is convenient and safe—it does not employ harmful radiation, and most therapy venues have ready access to ultrasound equipment and to trained technicians to use the equipment. However, image quality may be lower with ultrasound than with other imaging modalities; and ultrasound image quality may be impacted by the precise placement of the ultrasound transducer and by the skill of the ultrasound technician.

In some procedures, agitated saline (saline with microbubbles) may significantly enhance ultrasound guidance of needles used in musculoskeletal procedures. To underscore the need and benefit of any additional guidance that may be provided, various joints and indications are enumerated; then some detail is provided regarding a shoulder joint—an exemplary complex joint with many structures that must be navigated in an aspiration or injection procedure.

There are various indications for injections in an ankle, including, as examples, osteoarthritis, rheumatoid arthritis, acute traumatic arthritis, crystalloid deposition disease, mixed connective tissue disease, and synovitis. For the elbow, exemplary indications can include tennis elbow, arthritis and bursitis. For the hip: bursitis and arthritis. For the knee: osteoarthritis and bursitis. For the shoulder: rotator cuff disease (degenerative tendonitis, impingement, partial tears and subacromial bursitis), adhesive capsulitis ("frozen shoulder"), glenohumeral osteoarthritis, acromioclavicular joint disease (osteoarthritis or osteolysis) and bursitis. For the spine: chronic back pain, lumbar facet arthropathy, sacroiliac joint pain syndrome, arthritis and spondyloarthropathy. For the wrist and hand: carpal tunnel syndrome, first carpometacarpal joint disease, De Quervain's Tenosynovitis, ganglion cysts, and Trigger Finger. For the feet:

plantar fasciitis of the foot (heel spurs), Morton neuromas in the foot, gout and psoriatic arthritis.

Figure 1B:
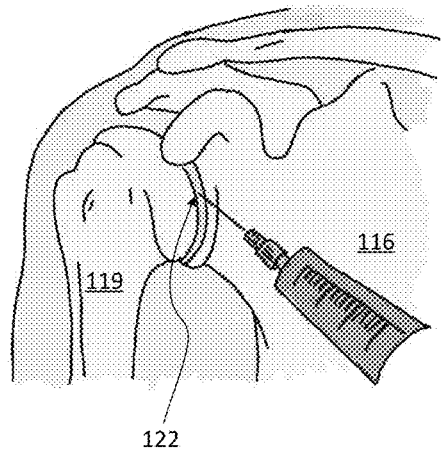
FIG. 1B depicts an exemplary injection into a glenohumeral joint.

In each of these cases, aspiration or injection requires careful positioning of a needle. This point is underscored with reference to FIGS. 1A, 1B and 1C. FIG. 1A. depicts an injection in the subacromial bursa 101. For reference, this bursa 101 (a fluid-filled sac or saclike cavity that counters friction at a joint) is disposed below the acromion 104 and next to the coracoacromial ligament 107. For reference, a number of additional anatomical features are noted in FIG. 1A, including the greater tuberosity of the humerus 110, the clavicle 113, the scapula 116, and the humerus 119. FIG. 1B depicts an injection into a different shoulder structure—namely, the glenohumeral joint 122.

Figure 1C:
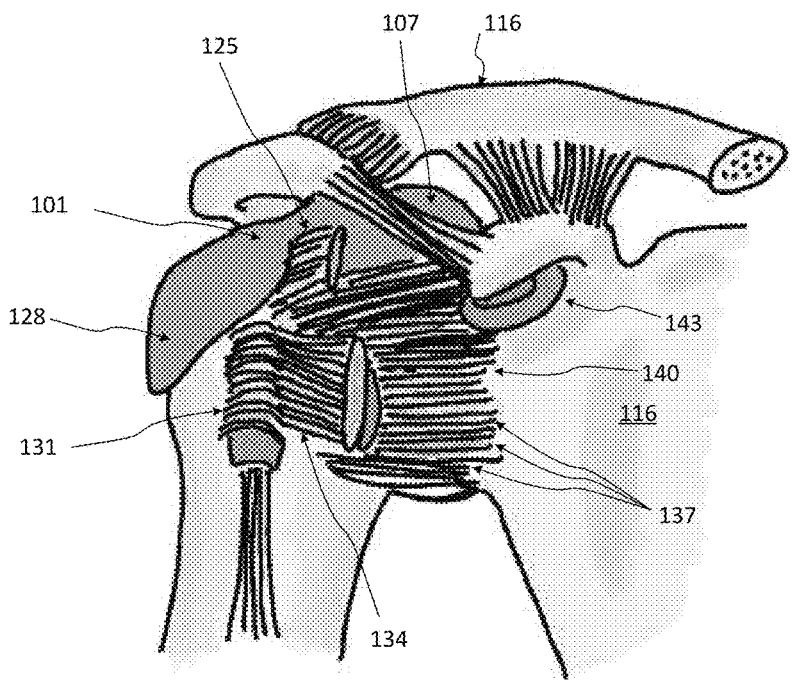
FIG. 1C illustrates exemplary structures adjacent a subacromial bursa and glenohumeral joint.

FIG. 1C provides additional anatomical detail around the subacromial bursa 101 and the glenohumeral joint 122—underscoring how carefully a needle must be navigated in the exemplary procedures depicted in FIG. 1A and FIG. 1B. In particular, the tendon of the supraspinatus muscle 125 (shown in partial cutaway for clarity) is anchored directly below the subacromial bursa 101; the subdeltoid bursa 128 is positioned adjacent the subacromial bursa 101; the transverse humeral ligament 131 is anchored below the subdeltoid bursa 128, and the tendon of subscapularis muscle 134 is adjacent. Over the glenohumeral joint (hidden in FIG. 1C) are the glenohumeral ligaments 137 and articular capsule 140; and nearby is the subcoracoid bursa 143.

As the reader will appreciate from FIGS. 1A, 1B and 1C, there are many ligaments, bursa, bones and tendons in very close proximity to structures of interest (e.g., the exemplary subacromial bursa 101 or glenohumeral joint 122 depicted in FIGS. 1A and 1B, respectively), around which a healthcare provider must carefully navigate a needle.

These specific structures are exemplary for the shoulder. Although a shoulder joint is complex, given its wide range of motion, elbows, wrists, knees, hips and ankles all have a similar array of ligaments, bursa, bones and tendons that must also be navigated around. The reader will appreciate that the concepts described herein can be extended to other joints and procedures.

Figure 2A:
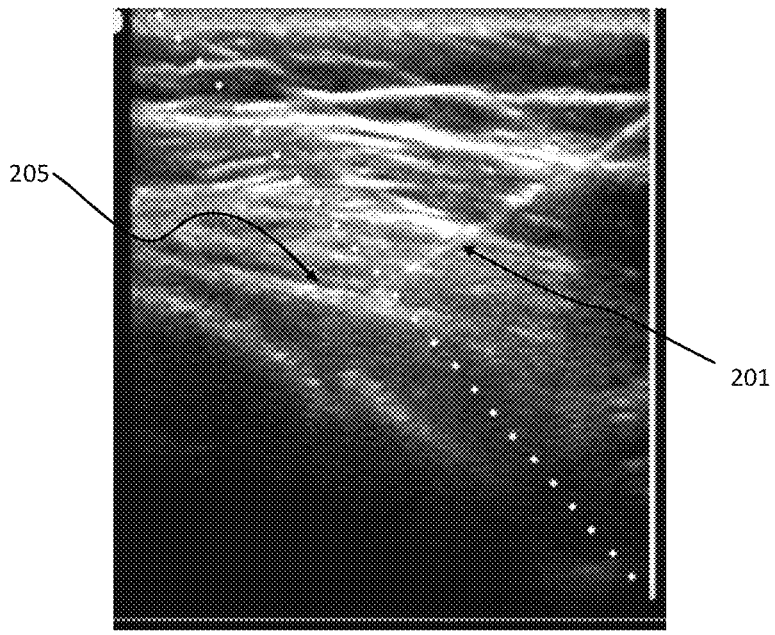
FIG. 2A depicts an exemplary ultrasound-guided procedure.

FIG. 2A illustrates exemplary ultrasound imaging that may be used to guide a needle during an injection or aspiration. As shown in the frame of FIG. 2A, various layers of tissue (muscle, ligaments, tendons, etc.) appear as contours. For example, the tissue plane 205 appears as a light-colored contour, given its hyperechogenic nature (ability to reflect ultrasound signals). In FIG. 2A, the needle 201 is partially visible, but its depth and the precise location of its tip are very difficult to identify. The reader will appreciate that even a skilled ultrasound technician must perform procedures very carefully—regularly pausing to confirm needle position by moving the ultrasound transducer and identifying anatomical landmarks on the screen. Even by doing this, the tip of the needle 201 may still be difficult to locate. If this tip is not in the desired spot when an aspiration is performed or an injection given, traumatic or catastrophic results may result (e.g., nerve damage, bone damage, tendon damage, etc.).

Figure 2B:
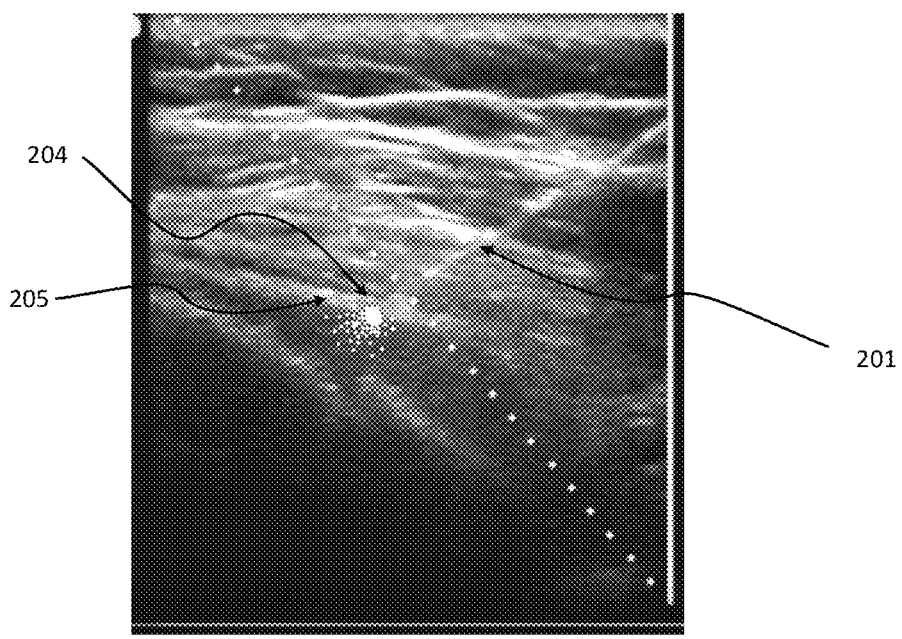
FIG. 2B depicts an exemplary ultrasound-guided procedure with bubbles.

FIG. 2B depicts the same ultrasound video as that of FIG. 2A, but with bubbles 204 employed to identify the tip of the needle 201. As depicted, a small amount of agitated saline has been injected through the needle 201. As shown, the bubbles 204 in the injected saline show up on the ultrasound image and provide an additional reference that may enable an ultrasound technician or healthcare provider to ascertain a more precise location of the tip. In addition, the bubbles 204, relative to other anatomical structures in the ultrasound image (e.g., the tissue plane 205), provide additional detail regarding location of the needle tip.

Small bubbles (e.g., microbubbles) in saline or similar solution may be superior to simply injecting a bolus of air into a patient. Their very small size enables them to be quickly absorbed into the surrounding tissue, without causing cramping or other issues in the patient. In addition, given the dispersion of the bubbles, they may more clearly indicate the location of the tip of needle, relative to layers of tissue (e.g., the tissue layer 205), whose depth may also be more clearly indicated by the bubbles.

Figure 3:
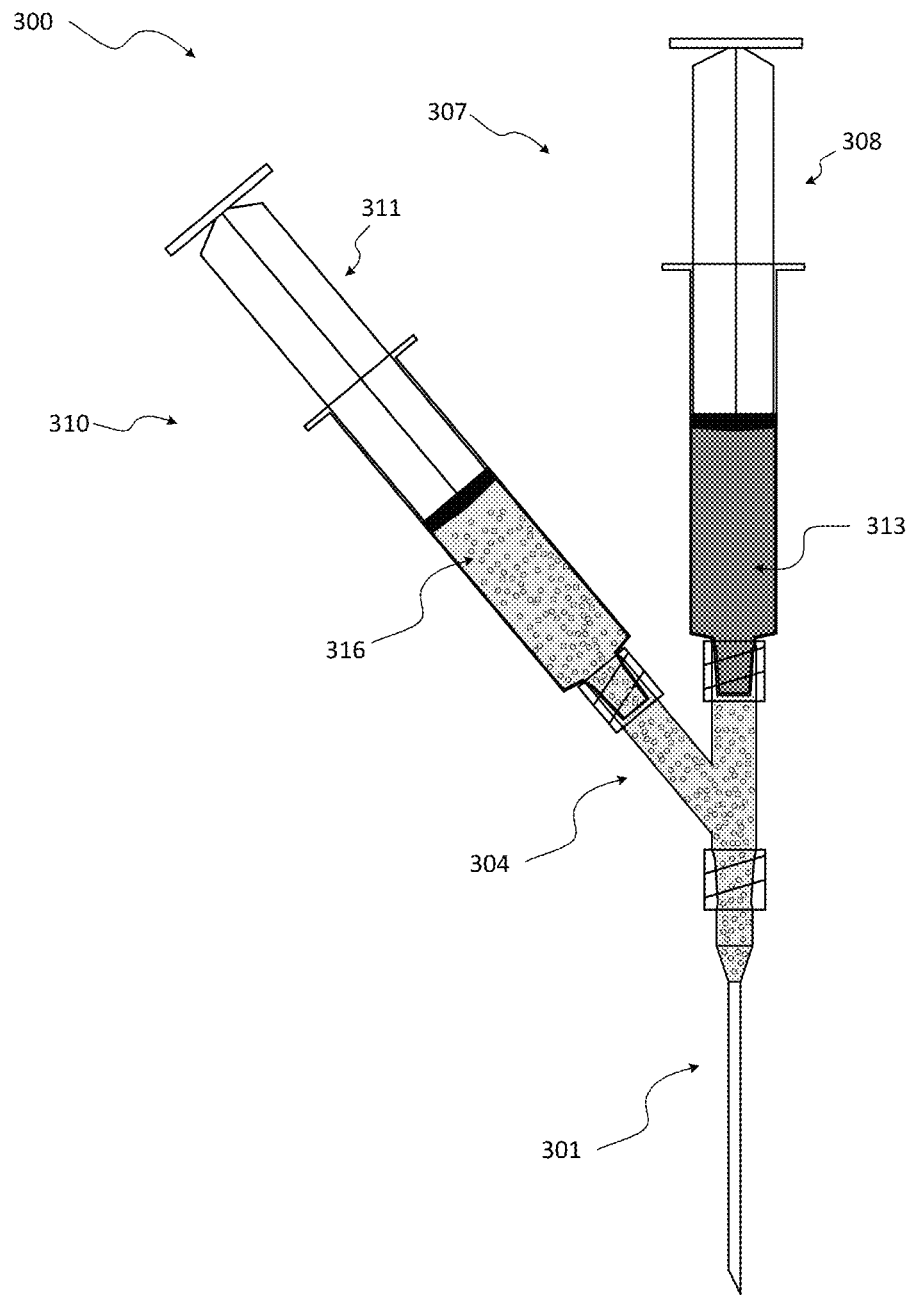
FIG. 3 illustrates an exemplary needle and syringe device.

FIG. 3 illustrates an exemplary needle and syringe device 300 that can deliver both bubbles and a therapeutic compound, such as corticosteroids, to, for example, a joint. As shown, the device 300 includes a single needle 301, a Y-connector 304 (as shown, with Luer lock connectors), a first syringe 310 having a first-syringe plunger 311, and a second syringe 307 having a second-syringe plunger 308. As shown, the first-syringe plunger 311 and second-syringe plunger 308 are independently operable. The first syringe 310 may contain an agitated saline 316 for injecting a small quantity of bubbles to help a medical care provider to place the needle 301, as described with reference to FIG. 2B; and the second syringe 307 may contain a corticosteroid 313, or other therapeutic compound, for injection into a patient's joint.

The device 300 illustrated in FIG. 3 is shown having two equally sized syringes coupled by a rigid Y-connector 304, but the device 300 could take other forms. For example, the agitated saline 316 could be coupled to the Y-connector 304 with flexible tubing to make the overall device 300 more easy to manipulate with one hand by a medical care provider who may be both operating the ultrasound transducer and performing an injection. The syringes 307 and 310 may be larger or smaller or differently sized. Rather than the needle 301 having a single lumen, it may be a double-lumen needle, and each lumen may be separately connected to a different syringe. Other variations are possible.

Figure 4:
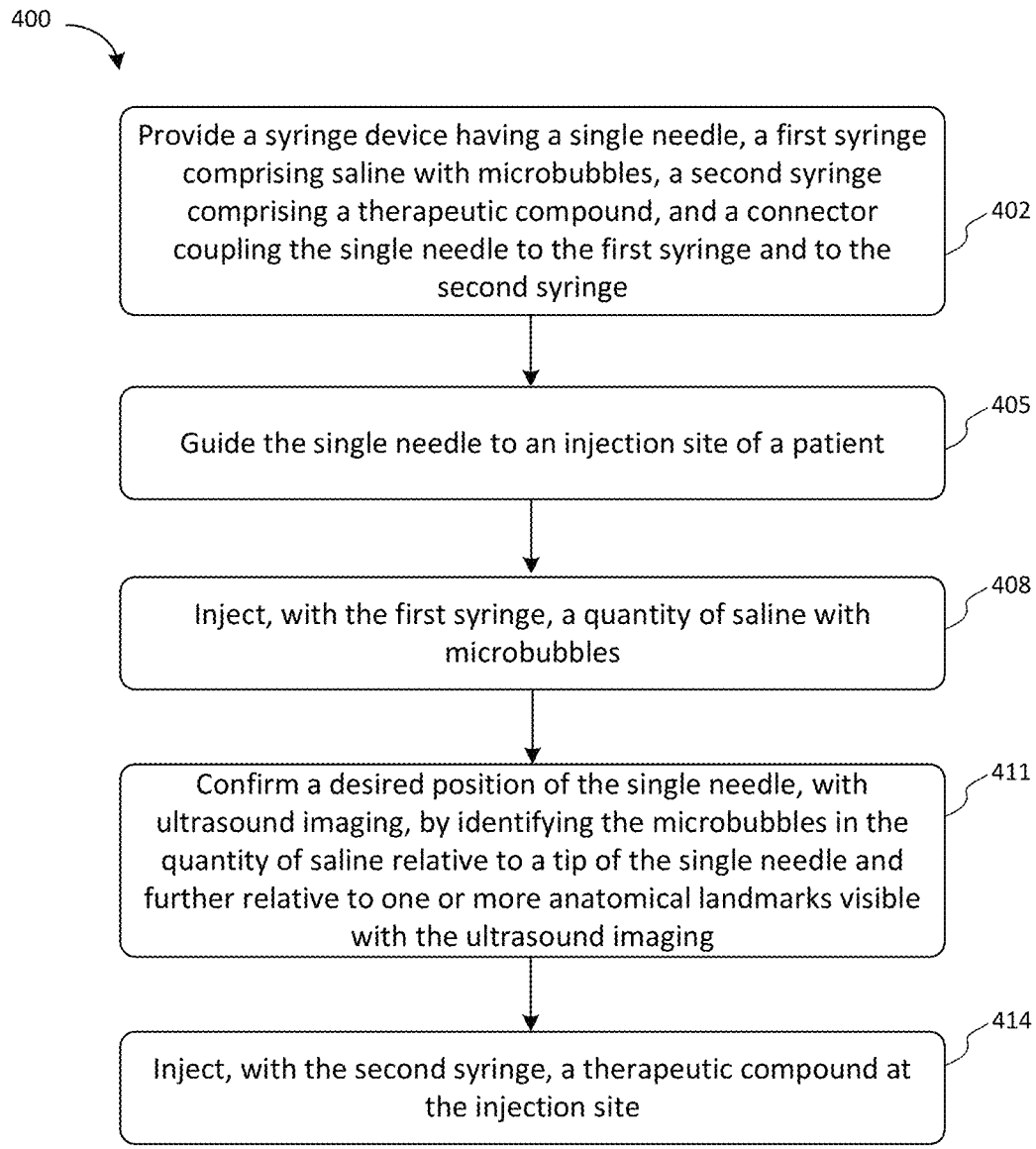
FIG. 4 illustrates an exemplary method for guiding injections.

FIG. 4 illustrates an exemplary method 400 for guiding injections. As illustrated, the method 400 includes providing (402) a syringe device. In particular, the method 400 includes providing (402) a syringe device having a single needle (e.g., the device 300, shown in FIG. 3, having a single needle 301), a first syringe comprising saline with microbubbles (e.g., syringe 310), a second syringe comprising a a therapeutic compound (e.g., syringe 310), and a connector coupling the single needle to the first syringe and second syringe (e.g., connector 304).

The method 400 may include guiding (405) the single needle to an injection site of a patient. For example, with reference to FIG. 1B, the method 400 may include guiding the single needle to the glenohumeral joint of a patient.

The method 400 may include injecting (408), with the first syringe, a quantity of saline with microbubbles. For example, with reference to FIG. 3, the method 400 could include injecting (408), e.g., by depressing the first-syringe plunger 311, to inject a quantity of saline with microbubbles.

The method 400 may include confirming (411) the desired position of the single needle, with ultrasound imaging. Confirming (411) the desired position of the single needle could include identifying microbubbles in the quantity of saline (via ultrasound imaging) relative to the tip of the single needle and further relative to one or more anatomical landmarks visible with the ultrasound imaging. For example, with reference to FIG. 2A, a portion of the needle 201 may be visible on ultrasound imaging, but a location of its tip may not be precisely known. After the quantity of saline with microbubbles is injected (408), the microbubbles may be visible on ultrasound, as depicted in FIG. 2B—enabling a clinician to confirm (411) desired location of the tip of the single needle.

The method 400 may include injecting (414), with the second syringe, a therapeutic compound at the injection site. For example, the method 400 may include injecting a therapeutic compound (e.g., by depressing the second-syringe plunger 308, to inject, for example, a corticosteroid 313 from the second syringe 307).

In many instances, the desired location will be relative to specific anatomic landmarks or structures—for example, in a bursa, such as the subacromial bursa 101, illustrated in FIG. 1A, or a joint, such as the glenohumeral join 122, illustrated in FIG. 1B. Such anatomic structures may be visible in ultrasound imaging (e.g., the tissue plane 205 shown in FIG. 2B), and the microbubbles may enable a clinician to confirm (411) location of the single needle relative to such structures.

Figure 5:
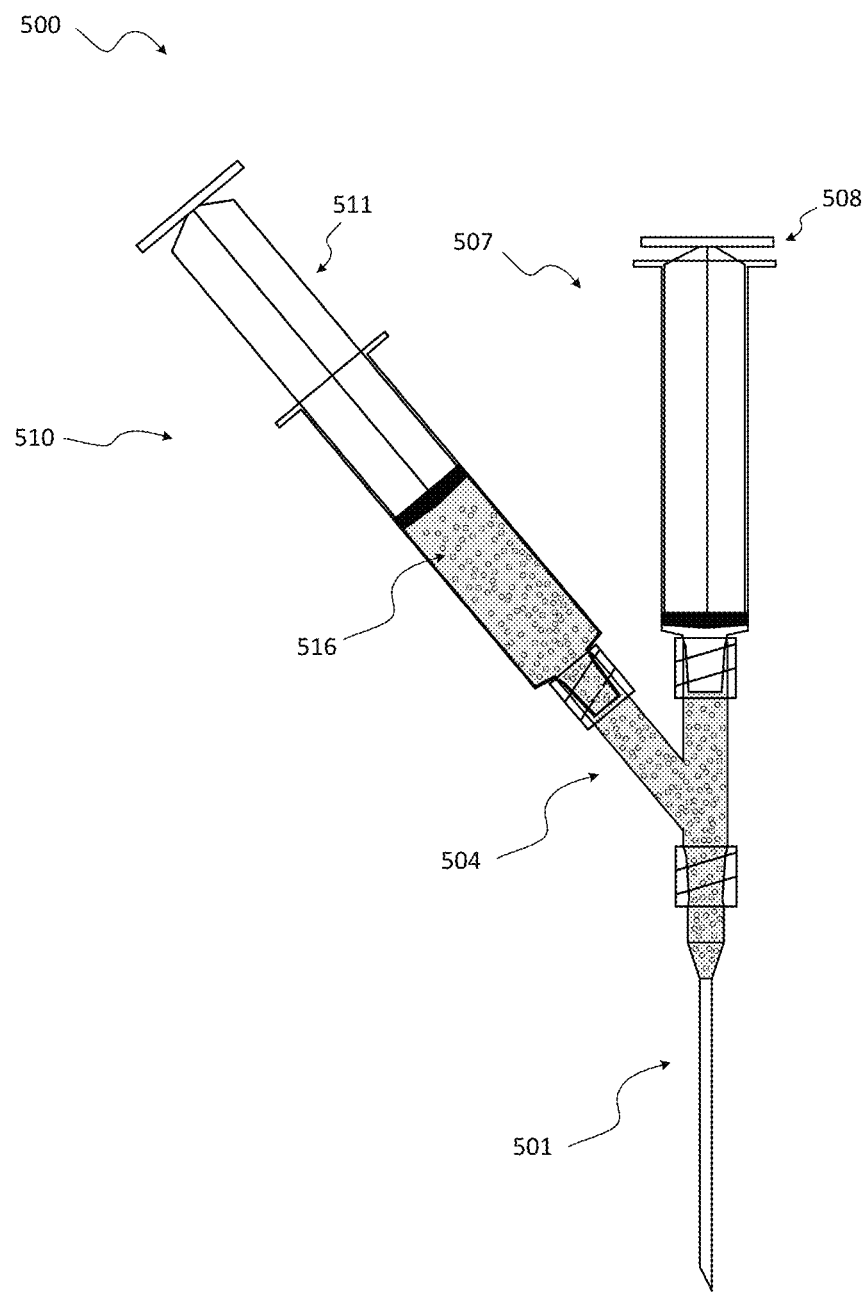
FIG. 5 illustrates another exemplary needle and syringe device.

FIG. 5 illustrates an exemplary needle and syringe device 500 that can be used to aspirate a joint. As shown, the device 500 includes a single needle 501, a Y-connector 504 (as shown, with Luer lock connectors), a first syringe 510 having a first-syringe plunger 511, and a second syringe 507 having a second-syringe plunger 508. The first syringe 510 may contain an agitated saline 516 for injecting a small quantity of bubbles to help a medical care provider to place the needle 501; and the second syringe 507 may be configured to aspirate fluid from a treatment site (e.g., the second syringe 507 may be empty, with its corresponding second-syringe plunger 508 fully depressed.

The device 500 illustrated in FIG. 5 is shown having two equally sized syringes coupled by a rigid Y-connector 504, but the device 500 could take other forms. For example, the agitated saline 516 could be coupled to the Y-connector 504 with flexible tubing to make the overall device 500 more easy to manipulate with one hand by a medical care provider who may be both operating the ultrasound transducer and performing an aspiration. The syringes 507 and 510 may be larger or smaller or differently sized. Rather than the needle 501 having a single lumen, it may be a double-lumen needle, and each lumen may be separately connected to a different syringe. Other variations are possible.

Figure 6:
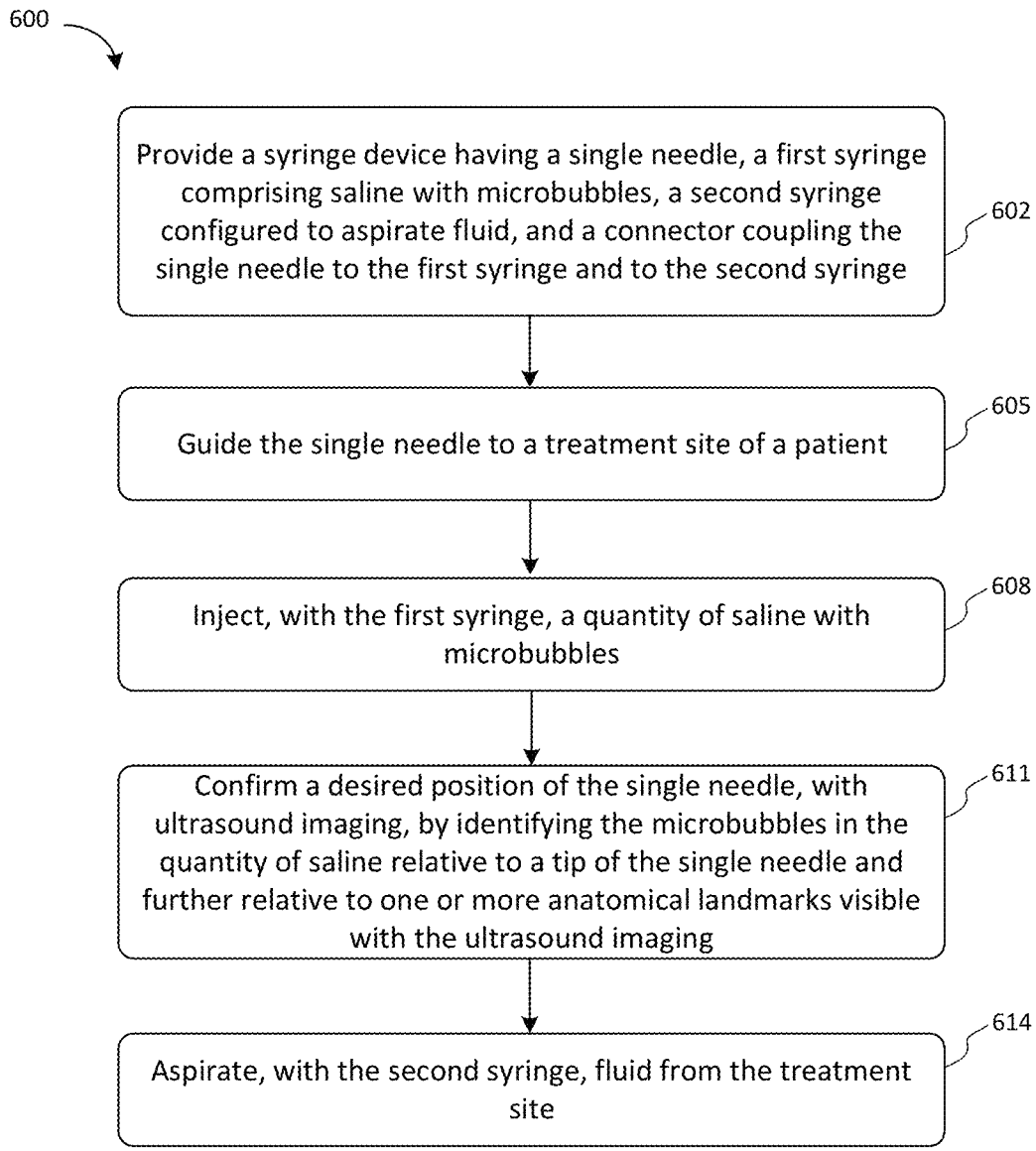
FIG. 6 illustrates an exemplary method for performing an aspiration.

FIG. 6 illustrates an exemplary method 600 for performing an aspiration. As illustrated, the method 600 includes providing (602) a syringe device. In particular, the method 600 includes providing (602) a syringe device having a single needle (e.g., the device 500, shown in FIG. 5, having a single needle 501), a first syringe comprising saline with microbubbles (e.g., syringe 510), a second syringe configured to aspirate fluid (e.g., syringe 507), and a connector coupling the single needle to the first syringe and second syringe (e.g., connector 504).

The method 600 may include guiding (605) the single needle to a treatment site of a patient. For example, with reference to FIG. 1B, the method 600 may include guiding the single needle to the glenohumeral joint of a patient.

The method 600 may include injecting (608), with the first syringe, a quantity of saline with microbubbles. For example, with reference to FIG. 5, the method 600 could include injecting (608), e.g., by depressing the first-syringe plunger 511, to inject a quantity of saline with microbubbles.

The method 600 may include confirming (611) the desired position of the single needle, with ultrasound imaging. Confirming (611) the desired position of the single needle could include identifying microbubbles in the quantity of saline (via ultrasound imaging) relative to the tip of the single needle and further relative to one or more anatomical landmarks visible through the ultrasound imaging. For example, with reference to FIG. 2A, a portion of the needle 201 may be visible on ultrasound imaging, but a location of its tip may not be precisely known. After the quantity of saline with microbubbles is injected (608), the microbubbles may be visible on ultrasound, as depicted in FIG. 2B—enabling a clinician to confirm (611) desired location of the tip of the single needle.

The method 600 may include aspirating (614), with the second syringe, fluid at the treatment site. For example, the method 600 may include aspirating (614) the glenohumeral joint of a patient by drawing back the second-syringe plunger 508, to aspirate the joint (e.g., to facilitate analysis of aspirated synovial fluid, to, for example, diagnose a joint infection).

In other implementations, devices and methods described herein can be employed to relieve pain. For example, in some implementations, a device may provide for delivery of air microbubbles mixed in saline or analgesic cocktails for use as a contrast agent for confirmation of needle placement in musculoskeletal injection procedures. The analgesic cocktails may include a mix of corticosteroids or visco-supplementation drugs such as lidocaine, betamethasone, epinephrine, and bupivacaine—which are low-viscosity. Musculoskeletal injections of anesthetics, corticosteroids, and lubricants may be used for therapeutic treatment of osteoarthritis, impingement syndromes and other clinical presentations like joint pain or reduced mobility—e.g., to relieve pain, reduce inflammation, and improve mobility.

In some implementations, standard of care may include confirming target delivery by palpation, aspiration, or by visualizing the needle tip directly within the anatomy using ultrasound. Other imaging modalities include fluoroscopy and computed tomography; however, ultrasound may be a preferred imaging modality due to its real-time feedback, procedural cost, and lack of ionizing radiation exposure. Other benefits of ultrasound as an imaging modality include reduction in procedural pain, reduction in absolute pain scores after the procedure, and increased detection of effusion.

Despite these advantages, ultrasound is an imperfect modality. In one survey, general practitioners reported low confidence in performing joint injections, with 95% regarding themselves as inadequately trained. Difficulty in needle placement can present a high barrier to performing musculoskeletal procedures, and needle placement accuracy can vary by caregiver and joint. For example, some groups have found needle placement accuracy using ultrasound as high as 80% in the sacroiliac joint, but others have found it to be only 50%. Without imaging, placement may be poor (e.g., 50-60% failure in some procedures). If the needle is not targeted correctly, the therapeutic benefit of the injection can be diminished, the injection itself may be more painful for the patient, and the provider may incorrectly diagnosis a condition because of not seeing an expected clinical response.

In some implementations, the devices and methods described herein can be employed to provide instantaneous feedback regarding injection location—which instantaneous feedback may be useful in training general practitioners and other providers (and increasing procedural confidence among the same) in performing musculoskeletal injections. By training such general practitioners and providers, patients who may otherwise need to visit a specialty center, may be able to access crucial therapy more readily.

Even among specialists, the devices and methods described herein can be beneficial. For example, certain joints such as the glenohumeral joint and the hip joint, are challenging targets both because of their depth and because the joint capsules are tightly attached via ligaments to the bone. Such structures can be especially difficult to navigate when the joint is deformed, when effusion or synovitis is present, or when the patient is obese. Hyaluronic acid can present a special challenge to inject because of poor physical feedback on injection pressure due to its viscosity; yet correct placement can be critical for hyaluronic acid to function effectively.

Needle placement confirmation techniques other than those described here may not be effective. For example, injection of saline alone prior to an analgesic or other substance may allow a provider to visualize distention of the joint when correctly placed, but it may be an insufficient indicator of misplaced injections. As another example, other chemical contrast agents (e.g., lipid coated microspheres such as SonoVue, Definity and Optison) may serve as effective contrast agents, but such agents can be cost-prohibitive for use in musculoskeletal procedures; moreover, some such contrast agents may require follow-on high-frequency ultrasound energy (e.g., to burst lipid coated microspheres) following an injection. As another example, injection of a small amount of air (typically about 5 mL) may help to verify needle placement. However, such air injections may cause image artifacts on ultrasound that can blind the provider for a substantial period of time (e.g., in some cases, 15-20 minutes—the time that may be required for tissue to absorb the injected air). If a provider misses a needle-placement-confirming injection of air, significant procedural delays and operating inefficiencies may result.

In contrast to the above-described alternatives, the devices and methods described herein can instantaneously produce microbubbles of air in saline or analgesic cocktails at a low cost and provide an effective contrast agent for confirmation of needle placement during ultrasound-guided musculoskeletal injections. In particular, in some implementations, the devices described herein can simplify musculoskeletal injections by providing air as a low cost, safe contrast agent that dissipates quickly; having a sleek and light form factor for easy guidance and placement of the needle single-handedly; and allowing the user to inject the contrast agent in a therapeutic cocktail, rather than separate from the therapeutic cocktail.

Figure 7:
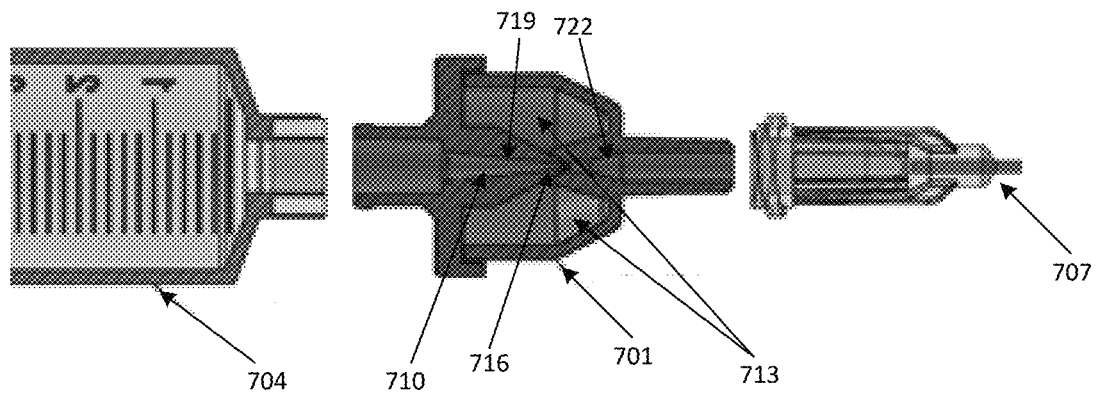
FIG. 7 illustrates an exemplary device that can be used with a standard drug-filled syringe and a standard injection needle.

Turning to FIG. 7, a user may employ an exemplary device 701 between a standard, drug-filled syringe 704 and a needle 707. As the fluid within the syringe 704 passes through the device 701, air microbubbles are generated in solution. If the needle 707 is placed in tissue, the microbubbles quickly dissipate (~15 seconds), restoring the ultrasound view and allowing the user to reposition the needle 707. If the needle 707 is placed correctly (e.g., intra-articularly), the microbubbles can delineate the edges of the joint for confirmation of placement of the needle 707.

Long-term benefits of such a device 701 can include improved access to musculoskeletal injections through a low cost, easily integrated microbubble contrast agent for use with injection therapeutic agents such as hyaluronic acid and lidocaine. While also important for specialists to use on difficult joints such as the glenohumeral or hip joint, the device 701 may also enable general practitioners or mid-level providers to perform musculoskeletal injections on joints such as the carpometacarpal joints of the hand or soft tissue injections into the Achilles tendon or to treat tendonitis. The device 701 may also be beneficial for other needle guidance applications, such as for confirmation of diagnostic contrast placement prior to MRI or X-Ray arthrography, placement within certain muscular planes, and for use in regional anesthesia.

In some implementations, an integrated aerator device may be employed, such as one of the devices described and illustrated in U.S. application Ser. No. 17/566,079, titled "Syringe-Based Microbubble Generator with an Aerator", filed Dec. 30, 2021, or U.S. application Ser. No. 17/542,386, titled "Syringe-Based Microbubble Generator," filed Dec. 4, 2021 (both of the foregoing applications are incorporated herein by reference). In other implementations, a device such as the device 701 shown in FIG. 7 may be employed. The device 701 may include features that are specifically designed for the viscosity and variation of the drug cocktails used in musculoskeletal injections, as well as the injection volumes and needle gauges (e.g., 22-25 gauge), the pressure environment within the joint, and the clinical needs of musculoskeletal injections. For example, the device 701 can contain vane structures in the exit nozzle to promote cavitation of the microbubbles in an environment of substantial backpressure in the tissue/joint environment. Furthermore, a length between the needle and exit nozzle may be increased to reduce the effects of backpressure from the needle due to the extra resistance to injection in joint cavities.

In some implementations, the device 701 may be available in different agitator sizes—for example, one size may be available for 5 mL injections, and another size may be available for a 10 mL injection volume. Other sizes may also be available. These sizes may differ in the volume of air injected. For example, the "agitator" can include an internal channel 710 that constricts the flow of fluid (e.g., saline, analgesic, or other therapeutic compound) to speed the fluid flow and, through the Venturi effect, withdraw air from a surrounding chamber 713 into the stream. Microbubbles can be formed by pulling air from the surrounding chamber 713 through the a throat 716 in the channel 710, between a converging nozzle 719 and diverging nozzle 722. As fluid is constricted in the converging nozzle 719, it enters the throat 716 at a greater velocity, and the static pressure lowers below the pressure in the chamber 713. Once the static pressure at the throat 716 surpasses the backpressure from the needle 707, microbubbles cavitate into the fluid stream.

Microbubble size from one implementation was analyzed using a laser diffraction and optical microscope. Production of microbubbles by another implementation were further analyzed in a cadaver study. The results of this analysis and these studies is now summarized.

Example 1

Figure 8A:
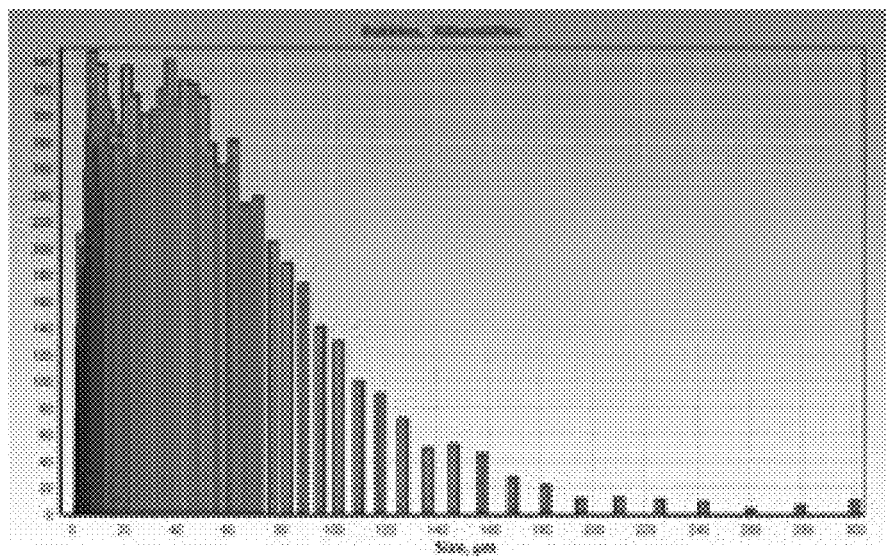
FIG. 8A illustrates results of a size-distribution analysis of microbubbles produced with an exemplary device.
Figure 8B:
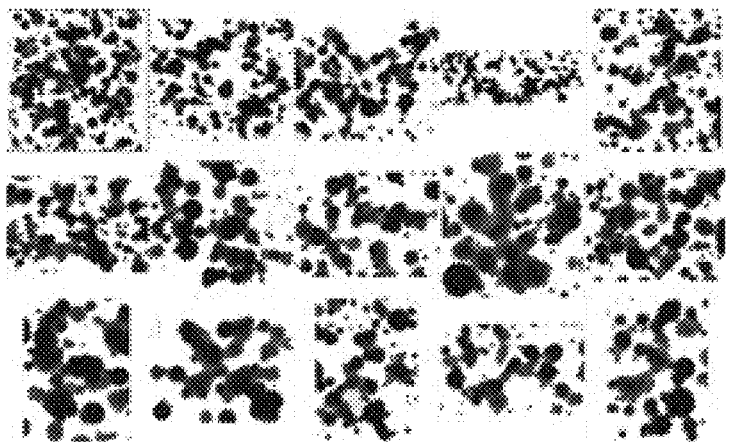
FIG. 8B illustrates optical microscope images of shapes of bubbles produced with an exemplary device.

In a first example, a microbubble size/distribution analysis was performed. In particular, a Coulter Multisizer and an Optical Microscope were placed in-line immediately following the site of injection from a device disposed in a water circulation loop to examine the size distribution and shape of the microbubbles generated. Distribution results from a single test are displayed in FIG. 8A. Three tests were conducted showing similar distributions, with an overall average microbubble size of 173 µm. Air microbubbles were numerous in the <80 µm range, which is clinically useful in two ways: (a) the microbubbles are expected to dissolve quickly so that visualization of the needle under ultrasound is restored faster, and (b) smaller microbubbles allow better delineation of the joint boundaries and anatomy under ultrasound. FIG. 8B illustrates optical microscope images showing air bubble shape in this example.

Example 2

In a second example, four cadaver hips were used in a comparison study to evaluate the echogenic potential of a device, like the device 701 shown in FIG. 7, with lidocaine or saline versus a bolus of air or saline. The device was provided in two sizes—one with 1 mL of air available for microbubble generation (e.g., with reference to FIG. 7, 1 mL of air in the chamber 713) and another with 2 mL of air available for microbubble generation.

Figure 9:
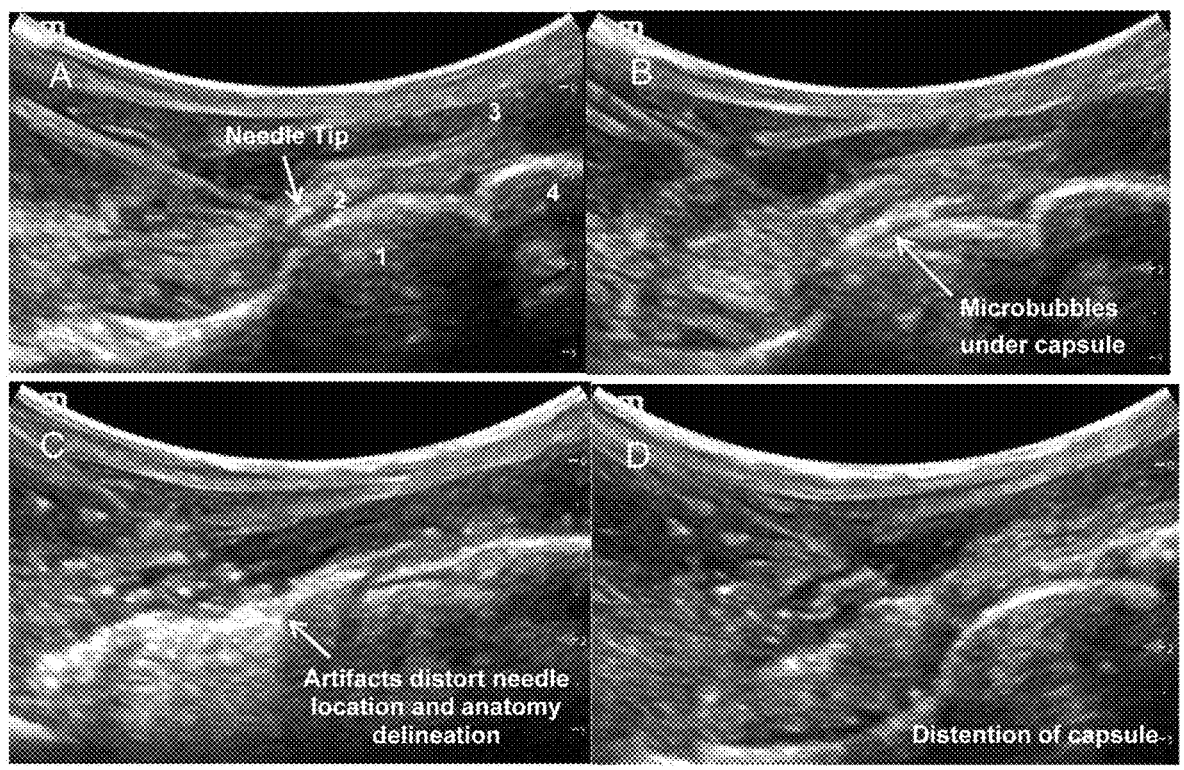
FIG. 9 illustrates selected images from a study involving hip injections performed with an exemplary device.

In a cadaver evaluation, a Mindray TE7 ultrasound device with a curved array transducer (L123 Probe) was operated at a 4-5 cm depth for an anterior approach hip injection with transverse probe placement. A Sports Medicine physician with a specialty in orthopedics and musculoskeletal evaluation and procedures, performed the injections under ultrasound. FIG. 9 contains selected images from a single hip injection in the cadaver study.

In FIG. 9, panel "A" (upper left), the anatomy prior to injection is shown. The anatomy visible here is the femur ("1"), the capsule ("2"), the Rectus Femoris ("3"), and the Acetabulum ("4"). The tip of the needle is also delineated in FIG. 9, panel "A". Generally, the objective of an injection in this joint is to place injectate beneath the capsule above the femur.

FIG. 9, panel "B" illustrates an injection with a device like the device 701 of FIG. 7. As shown, a stream of microbubbles is visible underneath the capsule indicating that the injection was accurately placed into the capsule. There was a steady number of microbubbles throughout the injection.

FIG. 9, panel "C" illustrates injection of a bolus of 1 mL of air into the space to evaluate the echogenicity of injecting air rather than microbubbles—which some clinicians utilize to visualize needle tip placement. The significant artifact on the image in panel "C" remained for about 20 minutes and obscured the needle tip location—illustrating the impracticality of using a bolus of air as a contrast agent in musculoskeletal injections.

FIG. 9, panel "D" illustrates a saline injection (without microbubble contrast). As shown, the only visible marker of the injection site is the distention of the capsule—a less appropriate and reliable tool for needle placement confirmation, especially for general practitioners or mid-level providers who are less familiar with specific joint anatomy.

Conclusion

While several implementations have been described with reference to exemplary aspects, it will be understood by those skilled in the art that various changes may be made and equivalents may be substituted for elements thereof without departing from the contemplated scope. For example, corticosteroids are provided as an example therapeutic compound; but other therapeutic compounds are also contemplated, such as, for example, local anesthetics (e.g., lidocaine, bupivacaine), hyaluronic acid or other viscosupplementation therapies to improve lubrication of joints, or other compounds for providing relief from joint issues or to promote healing of joint, muscle or ligament injuries (e.g., platelet rich plasma, or PRP; stem cells; nerve blocks, etc.).

In addition, many modifications may be made to adapt a particular situation or material to the teachings provided herein without departing from the essential scope thereof. Therefore, it is intended that the scope not be limited to the particular aspects disclosed but include all aspects falling within the scope of the appended claims.

What is claimed is:

1. A method comprising:
providing a device having a needle, a syringe comprising a therapeutic compound, and an aerator component disposed between the needle and the syringe; the aerator component comprising an internal channel and a chamber surrounding the internal channel; wherein the internal channel fluidly couples an interior of the syringe with an interior of the needle and is configured to constrict flow of fluid through the internal channel, thereby speeding flow of the fluid, and causing air from the chamber to be pulled into the fluid, thereby creating microbubbles;
guiding the needle to an injection site of a patient;
injecting, with the syringe, a quantity of the therapeutic compound through the aerator component to create microbubbles;
confirming a desired position of the single needle, with ultrasound imaging, by identifying the created microbubbles relative to a tip of the needle and further relative to one or more anatomical landmarks visible with the ultrasound imaging; and
injecting, with the syringe, additional therapeutic compound at the injection site.

2. The method of claim 1, wherein the therapeutic compound comprises a corticosteroid.

3. The method of claim 1, wherein the therapeutic compound comprises lidocaine.

4. The method of claim 1, wherein the therapeutic compound comprises hyaluronic acid.

5. The method of claim 1, wherein the injection site is a carpometacarpal joint of a patient.

6. The method of claim 1, wherein the injection site is an Achilles tendon of a patient.

7. The method of claim 1, wherein the injection site is a glenohumeral joint of a patient.

8. The method of claim 1, wherein the injection site is a hip joint of a patient.

9. The method of claim 1, wherein the therapeutic compound comprises at least one of anesthetics, corticosteroids or lubricants.

10. The method of claim 1, wherein the therapeutic compound comprises at least one of betamethasone, epinephrine or bupivacaine.

* * * * *